United States Patent [19]
Berger et al.

[11] 3,931,288
[45] Jan. 6, 1976

[54] ALKYL ESTERS OF 4-CHLOROPHENOXY-4-OXO-CYCLOALKYL-CARBOXYLIC ACID

[75] Inventors: Leo Berger; Willy Leimgruber, both of Montclair, N.J.; Fausto Eugenio Schenker, Riehen, Switzerland

[73] Assignee: Hoffmann-La Roche Inc., Nutley, N.J.

[22] Filed: Nov. 23, 1973

[21] Appl. No.: 418,713

Related U.S. Application Data

[60] Division of Ser. No. 234,375, March 13, 1972, Pat. No. 3,803,180, which is a continuation-in-part of Ser. No. 128,570, March 26, 1971, abandoned.

[52] U.S. Cl. ............................................ 260/473 G
[51] Int. Cl.² ........................................ C07C 69/76
[58] Field of Search ...................... 260/473 G, 520

[56] References Cited
OTHER PUBLICATIONS
Ganguly et al., C.A. 42 5003b.
Rene et al., C.A. 59 7527g.
Miles et al., C.A. 69 105979d.

*Primary Examiner*—John F. Terapane
*Attorney, Agent, or Firm*—Samuel L. Welt; Bernard S. Leon; William G. Isgro

[57] ABSTRACT

Tricyclic compounds of the formula

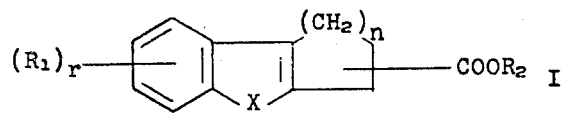

wherein $R_1$ is hydrogen, halogen, lower alkyl, lower alkoxy, lower alkylthio, trifluoromethyl, cyano, carbamoyl, carboxy, lower alkoxy carbonyl, nitro, amino, mono-lower alkylamino, di-lower alkylamino, acyl, acylamido, sulfamoyl, di-lower alkylsulfamoyl, or difluoromethylsulfonyl; $R_2$ is hydrogen, lower alkyl, amino-lower alkyl, mono-lower alkyl-amino-lower alkyl, or di-lower alkylamino-lower alkyl; $n$ and $r$ are independently 1 or 2; and X is oxygen or sulfur, prepared, inter alia, from the correspondingly substituted phenol or thiophenol and haloketocyclohexane or pentane carboxylic acid ester, are described. The end products are useful as anti-inflammatory and antirheumatic agents.

2 Claims, No Drawings

ALKYL ESTERS OF 4-CHLOROPHENOXY-4-OXO-CYCLOALKYL-CARBOXYLIC ACID

CROSS-REFERENCE TO RELATED APPLICATIONS

This is a division of application Ser. No. 234,375, filed March 13, 1972 now U.S. Pat. No. 3,803,180, which in turn is a continuation-in-part of U.S. Pat. application Ser. No. 128,570, filed Mar. 26, 1971, now abandoned.

BRIEF SUMMARY OF THE INVENTION

The invention relates to racemic compounds of the formula

I wherein $R_1$, independently, is hydrogen, halogen, lower alkyl, lower alkoxy, lower alkylthio, trifluoromethyl, cyano, carbamoyl, carboxy, lower alkoxy carbonyl, nitro, amino, mono-lower alkylamino, di-lower alkylamino, acyl, acylamido, sulfamoyl, di-lower alkylsulfamoyl, or difluoromethylsulfonyl; $R_2$ is hydrogen, lower alkyl, amino-lower alkyl, mono-lower alkylamino-lower alkyl or di-lower alkylamino-lower alkyl; $n$ and $r$ are independently 1 or 2; and X is oxygen or sulfur, their enantiomers, and when $R_1$ is carboxy and/or $R_2$ is hydrogen, salts thereof with pharmaceutically acceptable bases, and when $R_1$ is amino, mono-lower alkylamino or di-lower alkylamino, and/or when $R_2$ is amino-lower alkyl, mono-lower alkylamino-lower alkyl, or di-lower alkylamino-lower alkyl, addition salts thereof with pharmaceutically acceptable acids.

The compounds of formula I are useful as anti-inflammatory and anti-rheumatic agents.

In other aspects, the invention relates to intermediates of the formulas

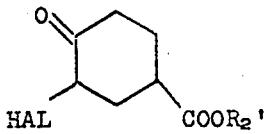

VIa

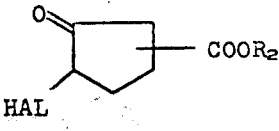

VIb

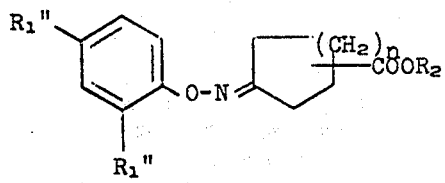

IV; and

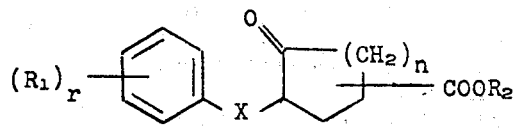

VII wherein $R_1$, $R_1''$, $R_2$, $R_2'$, $r$, $n$ and X are as herein described.

DETAILED DESCRIPTION OF THE INVENTION

As used herein, the term "lower alkyl" denotes a straight or branched chain hydrocarbon group containing 1–7 carbon atoms, for example, methyl, ethyl, propyl, isopropyl, butyl, isobutyl, tertiary butyl, neopentyl, pentyl, heptyl, and the like. The term "lower alkoxy" denotes an alkyl ether group in which the alkyl group is as described above, for example, methoxy, ethoxy, propoxy, isopropoxy, butoxy, pentoxy and the like. The term "lower alkylthio" denotes an alkylthio ether group in which the alkyl group is as described above, for example, methylthio, ethylthio, propylthio, isopropylthio, butylthio, pentylthio, and the like. The term "halogen" denotes all the halogens; that is, bromine, chlorine, fluorine and iodine; bromine and chlorine are preferred. The term "acyl" denotes an "alkanoyl" group derived from an aliphatic carboxylic acid of 1 to 7 carbon atoms, for example, formyl, acetyl, propionyl, and the like, and an "aroyl" group derived from an aromatic carboxylic acid, such as benzoyl and the like. Exemplary of acylamido are acetamido, benzylamido and the like. Exemplary of mono-lower alkylamino are methylamino, ethylamino and the like. Exemplary of di-lower alkylamino are dimethylamino, diethylamino and the like. Exemplary of amino-lower alkyl are aminomethyl, aminoethyl and the like. Exemplary of mono-lower alkylamino-lower alkyl are methylaminomethyl, ethylaminoethyl and the like. Exemplary of di-lower alkylamino-lower alkyl are dimethylaminomethyl, diethylaminoethyl and the like. Exemplary of di-lower alkylsulfamoyl are dimethylsulfamoyl, diethylsulfamoyl and the like.

The invention relates to racemic compounds of the formula

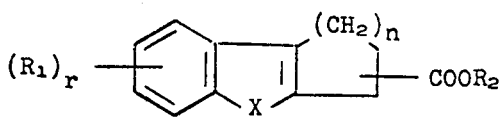    I wherein $R_1$ is hydrogen, halogen, lower alkyl, lower alkoxy, lower alkylthio, trifluoromethyl, cyano, carbamoyl, carboxy, lower alkoxycarbonyl, nitro, amino, mono-lower alkylamino, di-lower alkylamino, acyl, acylamido, sulfamoyl, di-lower alkylsulfamoyl or difluoromethylsulfonyl; $R_2$ is hydrogen, lower alkyl, amino-lower alkyl, mono-lower alkylamino-lower alkyl or di-lower alkylamino-lower alkyl; $n$ and $r$ are independently 1 or 2; and X is oxygen, sulfur, their enantiomers, and when $R_1$ is carboxy and/or $R_2$ is hydrogen, salts thereof with pharmaceutically acceptable bases, and when $R_1$ is amino, mono-lower alkylamino or di-lower alkylamino, and/or when $R_2$ is amino-lower alkyl, mono-lower alkylamino-lower alkyl, or di-lower alkylamino-lower alkyl, addition salts thereof with pharmaceutically acceptable acids.

A preferred sub-genus of the invention comprises racemic compounds of the formula

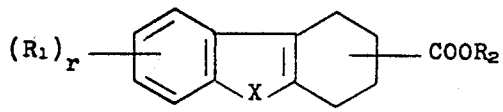    Ia wherein $R_1$, $R_2$, $r$ and X are as previously described, their enantiomers, and the respective salts thereof as herein described.

Preferred compounds of formula Ia comprise compounds of the formula

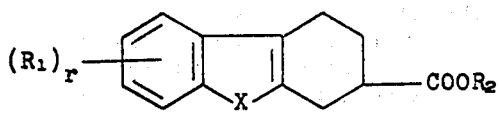    Ib wherein $R_1$, $R_2$, $r$ and X are as previously described, their enantiomers, and the respective salts thereof as herein described. Preferred compounds of formula Ib are those wherein X is oxygen.

Preferably, in formulas I, Ia and Ib, $R_1$ is hydrogen, halogen, lower alkyl, lower alkoxy, cyano, carboxy, lower alkoxycarbonyl, nitro, amino, mono-lower alkylamino, di-lower alkylamino, acyl or acylamido; and $R_2$ is hydrogen or lower alkyl.

The preferred compounds of the invention comprise compounds of the formula

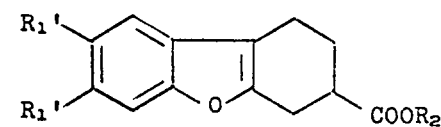    Ic wherein $R_2$ is as previously described, and $R_1'$ is independently hydrogen, chlorine or cyano, provided that at least one of $R_1'$ is hydrogen, their enantiomers and the respective salts thereof as herein described.

The most preferred compounds of the invention are:
8-chloro-1,2-dihydro-3(4H)-dibenzofurancarboxylic acid;
7-chloro-1,2-dihydro-3(4H)-dibenzofurancarboxylic acid; and
8-cyano-1,2-dihydro-3(4H)-dibenzofurancarboxylic acid.

Exemplary of the compounds of the invention corresponding to formula I wherein $n$ is 2 and X is oxygen are:
1,2-dihydro-3(4H),8-dibenzofurandicarboxylic acid;
8-acetyl-1,2-dihydro-3(4H)-dibenzofuran carboxylic acid;
8-amino-1,2-dihydro-3(4H)-dibenzofuran carboxylic acid;
8-amino-1,2-dihydro-3(4H)-dibenzofuran carboxylic acid ethyl ester;
7-amino-1,2-dihydro-3(4H)-dibenzofuran carboxylic acid ethyl ester;
7-amino-1,2-dihydro-3(4H)-dibenzofuran carboxylic acid;
8-chloro-1,2-dihydro-3(4H)-dibenzofuran carboxylic acid;
6-chloro-1,2-dihydro-3(4H)-dibenzofuran carboxylic acid;
9-chloro-1,2-dihydro-3(4H)-dibenzofuran carboxylic acid methyl ester;
9-chloro-1,2-dihydro-3(4H)-dibenzofuran carboxylic acid;
7-chloro-1,2-dihydro-3(4H)-dibenzofuran carboxylic acid;
1,2-dihydro-8-nitro-3(4H)-dibenzofuran carboxylic acid;
8-fluoro-1,2-dihydro-3(4H)-dibenzofuran carboxylic acid;
8-methyl-1,2-dihydro-3(4H)-dibenzofuran carboxylic acid;
7-acetamido-1,2-dihydro-3(4H)-dibenzofuran carboxylic acid ethyl ester;

7-acetamido-1,2-dihydro-3(4H)-dibenzofuran carboxylic acid;

1,2-dihydro-7-methoxy-3(4H)-dibenzofuran carboxylic acid;

7,9-dimethoxy-1,2-dihydro-3(4H)-dibenzofuran carboxylic acid;

7,9-dichloro-1,2-dihydro-3(4H)-dibenzofuran carboxylic acid;

8-cyano-1,2-dihydro-3(4H)-dibenzofuran carboxylic acid;

8-cyano-3,4-dihydro-1(2H)-dibenzofuran carboxylic acid;

8-carbamoyl-1,2-dihydro-3(4H)-dibenzofuran carboxylic acid ethyl ester;

8-cyano-3,4-dihydro-2(1H)-dibenzofuran carboxylic acid; and the like.

Exemplary of the compounds of the invention corresponding to formula I wherein $n$ is 1 and X is oxygen are:

2,3-dihydro-1H-cyclopenta[b]benzofuran-2-carboxylic acid;

7-chloro-2,3-dihydro-1H-cyclopenta[b]benzofuran-2-carboxylic acid;

7-acetyl-2,3-dihydro-1H-cyclopenta[b]benzofuran-2-carboxylic acid;

7-amino-2,3-dihydro-1H-cyclopenta[b]benzofuran-2-carboxylic acid;

7-amino-2,3-dihydro-1H-cyclopenta[b]benzofuran-2-carboxylic acid ethyl ester;

6-amino-2,3-dihydro-1H-cyclopenta[b]benzofuran-2-carboxylic acid;

5-chloro-2,3-dihydro-1H-cyclopenta[b]benzofuran-2-carboxylic acid;

6-chloro-2,3-dihydro-1H-cyclopenta[b]benzofuran-2-carboxylic acid;

8-chloro-2,3-dihydro-1H-cyclopenta[b]benzofuran-2-carboxylic acid;

7-nitro-2,3-dihydro-1H-cyclopenta[b]benzofuran-2-carboxylic acid;

7-fluoro-2,3-dihydro-1H-cyclopenta[b]benzofuran-2-carboxylic acid;

7-methyl-2,3-dihydro-1H-cyclopenta[b]benzofuran-2-carboxylic acid;

6-acetamido-2,3-dihydro-1H-cyclopenta[b]benzofuran-2-carboxylic acid;

6-acetamido-2,3-dihydro-1H-cyclopenta[b]benzofuran-2-carboxylic acid ethyl ester;

6-methoxy-2,3-dihydro-1H-cyclopenta[b]benzofuran-2-carboxylic acid;

6,8-dimethoxy-2,3-dihydro-1H-cyclopenta[b]benzofuran-2-carboxylic acid;

6,8-dichloro-2,3-dihydro-1H-cyclopenta[b]benzofuran-2-carboxylic acid;

7-cyano-2,3-dihydro-1H-cyclopenta[b]benzofuran-2-carboxylic acid;

7-carbamoyl-2,3-dihydro-1H-cyclopenta[b]benzofuran-2-carboxylic acid, and the like.

Exemplary of the compounds of the invention corresponding to formula I wherein $n$ is 2 and X is sulfur are:

1,2-dihydro-3(4H)-dibenzothiophene carboxylic acid;

8-chloro-1,2-dihydro-3(4H)-dibenzothiophene carboxylic acid ethyl ester;

8-chloro-1,2-dihydro-3(4H)-dibenzothiophene carboxylic acid;

8-acetyl-1,2-dihydro-3(4H)-dibenzothiophene carboxylic acid;

8-amino-1,2-dihydro-3(4H)-dibenzothiophene carboxylic acid;

8-amino-1,2-dihydro-3(4H)-dibenzothiophene carboxylic acid ethyl ester;

7-amino-1,2-dihydro-3(4H)-dibenzothiophene carboxylic acid;

7-amino-1,2-dihydro-3(4H)-dibenzothiophene carboxylic acid methyl ester;

8-chloro-1,2-dihydro-3(4H)-dibenzothiophene carboxylic acid;

6-chloro-1,2-dihydro-3(4H)-dibenzothiophene carboxylic acid;

9-chloro-1,2-dihydro-3(4H)-dibenzothiophene carboxylic acid; 9-chloro-1,2-dihydro-3(4H)-dibenzothiophene carboxylic acid propyl ester;

7-chloro-1,2-dihydro-3(4H)-dibenzothiophene carboxylic acid;

8-nitro-1,2-dihydro-3(4H)-dibenzothiophene carboxylic acid;

8-fluoro-1,2-dihydro-3(4H)-dibenzothiophene carboxylic acid;

8-methyl-1,2-dihydro-3(4H)-dibenzothiophene carboxylic acid;

7-acetamido-1,2-dihydro-3(4H)-dibenzothiophene carboxylic acid;

7-acetamido-1,2-dihydro-3(4H)-dibenzothiophene carboxylic acid methyl ester;

7-methoxy-1,2-dihydro-3(4H)-dibenzothiophene carboxylic acid;

7,9-dimethoxy-1,2-dihydro-3(4H)-dibenzothiophene carboxylic acid;

7,9-dichloro-1,2-dihydro-3(4H)-dibenzothiophene carboxylic acid;

8-cyano-1,2-dihydro-3(4H)-dibenzothiophene carboxylic acid;

8-carbamoyl-1,2-dihydro-3(4H)-dibenzothiophene carboxylic acid, and the like.

Exemplary of the compounds of the invention corresponding to formula I wherein $n$ is 1 and X is sulfur are:

2,3-dihydro-1H-cyclopenta[b][1]benzothiophene-2-carboxylic acid;

7-chloro-2,3-dihydro-1H-cyclopenta[b][1]benzothiophene-2-carboxylic acid; 7-acetyl-2,3-dihydro-1H-cyclopenta[b][1]benzothiophene-2-carboxylic acid;

7-amino-2,3-dihydro-1H-cyclopenta[b][1]benzothiophene-2-carboxylic acid;

7-amino-2,3-dihydro-1H-cyclopenta[b][1]benzothiophene-2-carboxylic acid ethyl ester;

6-amino-2,3-dihydro-1H-cyclopenta[b][1]benzothiophene-2-carboxylic acid;

5-chloro-2,3-dihydro-1H-cyclopenta[b][1]benzothiophene-2-carboxylic acid;

6-chloro-2,3-dihydro-1H-cyclopenta[b][1]benzothiophene-2-carboxylic acid;

8-chloro-2,3-dihydro-1H-cyclopenta[b][1]benzothiophene-2-carboxylic acid;

7-nitro-2,3-dihydro-1H-cyclopenta[b][1]benzothiophene-2-carboxylic acid;

7-fluoro-2,3-dihydro-1H-cyclopenta[b][1]benzothiophene-2-carboxylic acid;

7-methyl-2,3-dihydro-1H-cyclopenta[b][1]benzothiophene-2-carboxylic acid;

6-acetamido-2,3-dihydro-1H-cyclopenta[b][1]benzothiophene-2-carboxylic acid;

6-acetamido-2,3-dihydro-1H-cyclopenta[b][1]benzothiophene-2-carboxylic acid ethyl ester;

6-methoxy-2,3-dihydro-1H-cyclopenta[b][1]benzothiophene-2-carboxylic acid;
6,8-dimethoxy-2,3-dihydro-1H-cyclopenta[b][1]benzothiophene-2-carboxylic acid;
6,8-dichloro-2,3-dihydro-1H-cyclopenta[b][1]benzothiophene-2-carboxylic acid;
7-cyano-2,3-dihydro-1H-cyclopenta[b][1]benzothiophene-2-carboxylic acid;
7-carbamoyl-2,3-dihydro-1H-cyclopenta[b][1]benzothiophene-2-carboxylic acid, and the like.

The preparation of compounds of formula I wherein $n$ is 1 or 2 and X is oxygen is exemplified by Reaction Scheme I.

perature of the reaction mixture. The molar ratio of the reactants is not critical. Preferably, they are reacted in a 1:1 molar ratio.

The oxime of formula IV is converted to the compound of formula Id utilizing, for example, an acidic catalyst such as an organic, inorganic or Lewis acid, exemplary of which are hydrochloric acid, sulfuric acid, phosphoric acid, zinc chloride, copper chloride, boron trifluoride and the like, and various combinations thereof. Conveniently, the reaction can be carried out in a polar solvent such as an alkanol, for example, methanol, ethanol, propanol, and the like, water or a hydrocarbon such as benzene, toluene and the like.

Scheme I

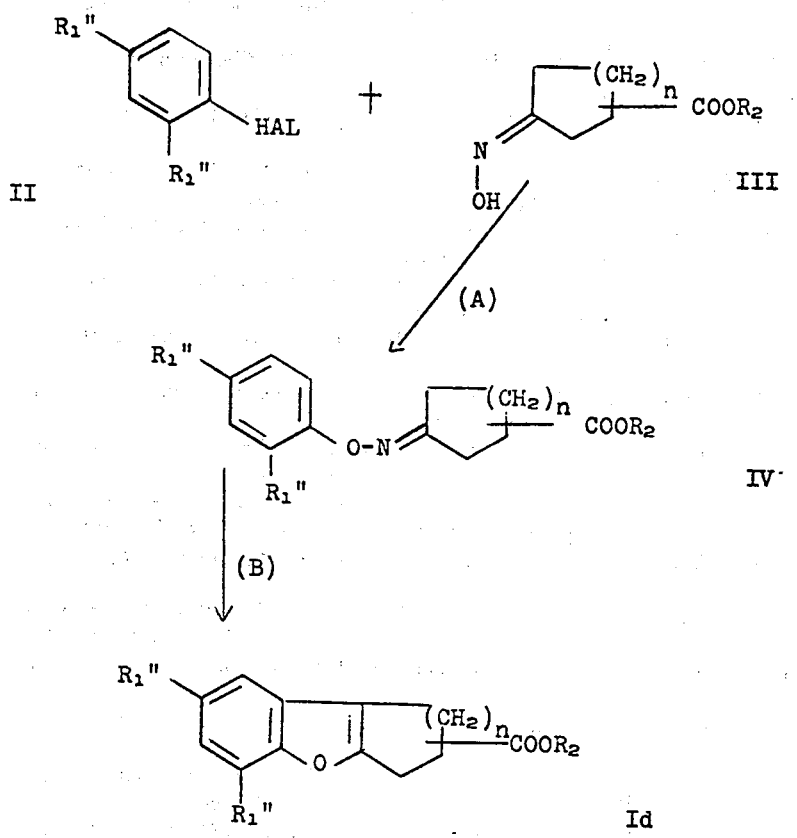

wherein HAL is halogen, for example, chlorine, fluorine, bromine and iodine, preferred is fluorine; $R_1''$ is hydrogen or an electron withdrawing group such as nitro, trifluoromethyl, lower alkoxy carbonyl, cyano or acyl, provided that at least one of $R_1''$ is other than hydrogen, and $R_2$ and $n$ are as described herein.

In Reaction Scheme I, the reaction of a halobenzene of formula II with an oxime of formula III to yield an O-phenyl oxime of formula IV is conveniently carried out in a polar solvent, such as dimethylsulfoxide, dimethylformamide, or hexamethylphosphoric triamide. The reaction temperature is not critical. Preferably, the reaction is carried out at a temperature in the range of from about room temperature to about the reflux temperature of the reaction mixture. The separation of the desired compound of formula Id from the reaction mixture can be effected utilizing known techniques such as, for example, filtration, crystallization, distillation and the like.

A nitro group present in the compound of formula Id can be converted to an amino group utilizing known procedures, for example, by catalytic reduction. An amino group can be converted to a diazonium salt utilizing known procedures, for example, by reaction with sodium nitrite and a mineral acid such as a hydrohalic acid. A diazonium group can then be replaced by a halogen, cyano, hydroxy, lower alkoxy or hydrogen utilizing known procedures, for example, by mixing a diazonium salt solution with, for example, a cuprous halide, cuprous cyanide, water, an alkanol or a reducing agent, such as hypophosphorous acid, respectively, at room temperature or occasionally at elevated temperatures.

The preparation of compounds of formula I is also exemplified by Reaction Scheme II.

like. Preferably, the reaction is carried out at a temperature in the range of from about −20° to about 120°. The reaction can be conveniently carried out with or without a solvent. Exemplary of convenient solvents are acetic and the like.

The esters of formula Ie can be converted to the corresponding acid, i.e., the compounds of formula I wherein $R_2$ is hydrogen, by saponification according to known procedures, for example, by reaction with an alkali metal hydroxide such as sodium hydroxide, po-

Scheme II

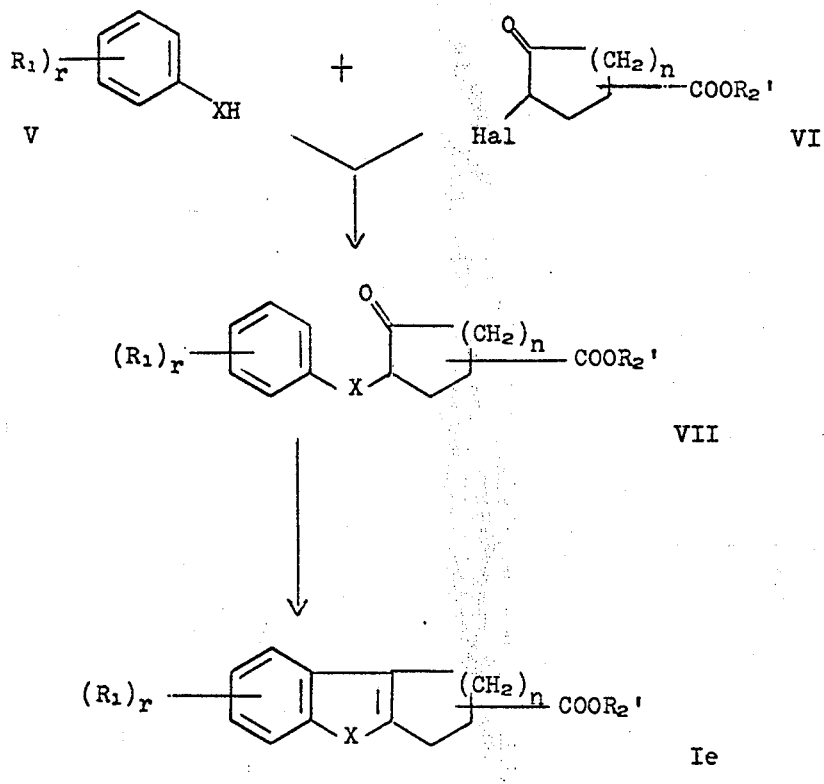

wherein $R_1$, X, n and r are as previously described, and $R_2'$ is lower alkyl.

In Reaction Scheme II, a compound of formula V is alkylated with the corresponding haloketocycloalkane carboxylic acid ester of formula VI to yield a compound of formula VII. The reaction is conveniently carried out in a non-polar solvent, for example, a hydrocarbon, such as benzene, toluene and the like, or a polar solvent, such as dimethylsulfoxide, dimethylformamide, hexamethylphosphoric triamide, and the like. The reaction temperature is not critical. Preferably, the reaction is carried out at a temperature in the range of from about room temperature to about the reflux temperature of the reaction mixture. The molar ratio of the reactants is not critical. Preferably, they are reacted at a 1:1 molar ratio.

A compound of formula VII is converted to a compound of formula Ie by thermal cyclization or by utilizing a cyclizing agent, such as polyphosphoric acid, sulfuric acid, acetic acid, hydrochloric acid, and the tassium hydroxide and the like, and subsequent treatment with a mineral acid, for example, a hydrohalic acid, such as hydrochloric acid and the like.

The separation of the desired compound of formula Ie and its corresponding acid from the reaction mixture can be effected utilizing known techniques such as, for example, filtration, crystallization, distillation and the like.

Furthermore, a salt of an acid of formula I, i.e., a salt of compounds of formula I wherein $R_2$ is hydrogen, can be converted to a compound of formula I wherein $R_2$ is amino-lower alkyl, mono-lower alkylamino-lower alkyl or di-lower alkylamino-lower alkyl by known procedures. For example, a salt of an acid of formula I is reacted with a amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

The starting materials of formula II are known compounds or can be prepared in an analogous manner to known compounds. Exemplary of such compounds are:
 4-fluoronitrobenzene;
 4-fluorocyanobenzene;
 4-fluoroacetophenone; and the like.

The starting materials of formula III are known compounds or can be prepared in an analogous manner to known compounds. Exemplary of such compounds are:
 3-oxyiminocyclohexanecarboxylic acid methyl ester;
 4-oxyiminocyclohexanecarboxylic acid ethyl ester;
 2-oxyiminocyclohexanecarboxylic acid methyl ester;
 3-oxyiminocyclopentanecarboxylic acid propyl ester;
 2-oxyiminocyclopentanecarboxylic acid methyl ester;
 4-oxyiminocyclopentanecarboxylic acid methyl ester; and the like.

The intermediates of formula IV are novel compounds. Exemplary of such compounds are:
 3-(4-nitrophenoxyimino)cyclohexanecarboxylic acid and methyl ester thereof;
 3-(2-nitrophenoxyimino)cyclohexanecarboxylic acid and methyl ester thereof;
 3-(4-cyanophenoxyimino)cyclohexanecarboxylic acid;
 3-(2-trifluoromethylphenoxyimino)cyclohexanecarboxylic acid;
 2-(4-nitrophenoxyimino)cyclopentanecarboxylic acid and methyl ester thereof;
 2-(4-cyanophenoxyimino)cyclopentanecarboxylic acid and methyl ester thereof; and the like.

The starting materials of formula V are known compounds or can be prepared in an analogous manner to known compounds. Exemplary of such compounds are:
 4-chlorophenol;
 5-chlorophenol;
 4-nitrophenol;
 p-cresol;
 4-chlorothiophenol The starting materials of formula VI can be prepared as exemplified in Reaction Scheme III:

dures, for example, utilizing a halogen such as bromine in ether, at a temperature of −10°C. Exemplary of such compounds are:
 3-bromo-4-ketocyclohexanecarboxylic acid;
 3-bromo-4-ketocyclohexanecarboxylic acid ethyl ester;
 2-bromo-3-ketocyclohexanecarboxylic acid;
 4-bromo-5-ketocyclohexanecarboxylic acid;
 3-bromo-4-ketocyclopentanecarboxylic acid;
 3-bromo-4-ketocyclopentanecarboxylic acid ethyl ester;
 2-bromo-3-ketocyclopentanecarboxylic acid;
 4-bromo-5-ketocyclopentanecarboxylic acid, and the like.

The intermediates of formula VII are novel compounds. Exemplary of such compounds are:
 3(4-chloro-phenoxy)-4-oxo-cyclohexane-carboxylic acid and ethyl ester thereof;
 3-(4-chloro-phenylthio)-4-oxo-cyclohexane-carboxylic acid and ethyl ester thereof;
 3-(4-chloro-phenoxy)-4-oxo-cyclopentane-carboxylic acid and methyl ester thereof;
 3-(4-chloro-phenylthio)-4-oxo-cyclopentane-carboxylic acid and methyl ester thereof; and the like.

The compounds of formula I, when R is amino, mono-lower alkylamino or di-lower alkylamino, and/or when $R_2$ is aminolower alkyl, mono-lower alkylamino-lower alkyl or di-lower alkylamino-lower alkyl, form addition salts with pharmaceutically acceptable organic or inorganic acids such as hydrohalides, e.g., hydrochloride, hydrobromide, hydroiodide, other mineral acid salts such as sulfate, nitrate, phosphate and the like, alkyl- and mono-aryl sulfonates such as ethanesulfonate, toluene-sulfonate, benzenesulfonate, or the like, other organic acid salts, such as acetate, tartrate, maleate, citrate, benzoate, salicylate, ascorbate and the like.

The compounds of formula I, when $R_1$ is carboxy and/or $R_2$ is hydrogen, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium etholate, potassium etholate and the like; organic bases such as piperidine, diethanolamine, N-methylglucamine and the like. Also included are the aluminum salts of the compounds of formula I, when $R_1$ is carboxy and/or $R_2$ is hydrogen.

Scheme III

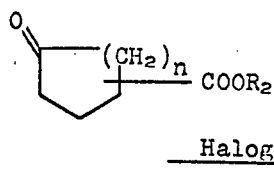 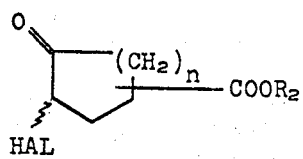

VIII → Halogenation → VI

The compounds of formula VIII are known compounds or can be prepared in an analogous manner to known compounds.

The halogenation is effected utilizing known proce-

The compounds of formula I, including the salts of those compounds of formula I which form salts with pharmaceutically acceptable bases and acids, possess anti-inflammatory activity and anti-rheumatic activity, and are therefore useful as antiinflammatory agents and anti-rheumatic agents. Their pharmacologically useful activities are demonstrated in warmblooded animals using standard procedures.

For example, the anti-inflammatory activity is demonstrated in Albino rats of Hart Strain, weighing 125-155 gms. The test animals are given 10 ml. of vehicle[1], which contains the test compound per kg. of body weight. The animals are treated daily for 5 consecutive days. Three hours after the first treatment, 0.05 ml. of an 0.5 percent suspension of heat killed dessiccated *Mycobacterium butyricum* in U.S.P. olive oil, which has been steam sterilized for 30 minutes, is injected into the right hind foot of each rat. The paw volume is measured immediately after the injection of the adjuvant and again 96 hours later. The difference is recorded as volume of edema. The paw volume is measured by immersion of the paw into a column of mercury to an ink mark exactly at the level of the lateral malleolus. Percent inhibition is calculated by dividing the average control edema minus the average treatment edema by the average control edema times 100. The percent inhibition is plotted against dose on semilogarithmic probability paper and the dose required to produce a 30 percent reduction in edema is estimated therefrom and is expressed as $ED_{30}$.

[1]Hilgar, A. G. and Hummel, D. J.: Endocrine Biossay Data, No. 1, p. 15, August 1964 (Cancer Chemotherapy National Service Center, N.I.H.)

When 7-chloro-1,2-dihydro-3-(4H)-dibenzofuran carboxylic acid is utilized as the test substance at a dosage of 11.5 mg. p.o., an anti-inflammatory activity is observed ($ED_{30} = 11.5$).

The compounds of formula I, their enantiomers and salts as herein described, have effects qualitatively similar to those of phenylbutazone, known for its therapeutic uses and properties. Thus, the compounds of this invention demonstrate a pattern of activity associated with anti-inflammatory agents of known efficacy and safety.

The compound of formula I, their enantiomers and salts as herein described can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene-glycols and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

Since the compounds of the invention possess asymmetric carbon atoms, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active base, such as d-α-(1-naphthyl)ethylamine, which can be reacted with the carboxyl group. The formed diastereomers are separated by selective crystallization and converted to the corresponding optical isomer. Thus, the invention covers the racemates of the compounds of formula I as well as their optically active isomers.

The following examples further illustrate the invention. All temperatures are in degrees Centigrade, unless otherwise mentioned.

EXAMPLE 1

Preparation of 3-(4-nitrophenoxyimino)cyclohexanecarboxylic acid

A mixture of 12.1 g. of potassium t-butoxide and 8.5 g. of 3-oxyiminocyclohexanecarboxylic acid in 90 ml. of dimethylsulfoxide was treated with 5.73 ml. of 4-fluoronitrobenzene, stirred vigorously at room temperature for two hours, diluted with 450 ml. of saturated sodium chloride solution and acidified with acetic acid. The precipitate was removed by filtration, washed successively with water and pentane, and dried to give 14.25 g. of 3-(4-nitrophenoxyimino)-cyclohexanecarboxylic acid as light yellow crystals, m.p. 146°–151° dec. This material can be used for the next step without purification. Recrystallized from methylene chloride ether, 3-(4-nitrophenoxyimino)cyclohexanecarboxylic acid has a melting point of 158.5°–159° dec.

Analysis calcd. for $C_{13}H_{14}N_2O_5$ (278.26): C, 56.11; H, 5.07; N, 10.07. Found: C, 56.42; H, 5.08; N, 10.37.

EXAMPLE 2

Preparation of 1,2-dihydro-8-nitro-3(4H)-dibenzofurancarboxylic acid

A solution of 23.4 g. of 3-(4-nitrophenoxyimino)cyclohexanecarboxylic acid in 250 ml. of acetic acid containing 29 g. of hydrogen chloride was stirred at 90° for 17 hours. Thereafter, the reaction mixture was cooled to 30° and filtered. The solid residue was washed successively with acetic acid, hexane and water, and dried to give 8.5 g. of 1,2-dihydro-8-nitro-3(4H)-dibenzofurancarboxylic acid as tan crystals, m.p. 229°–231.5°. This material can be used for the next step without purification. Recrystallized from acetone-ether, 1,2-dihydro-8-nitro-3(4H)-dibenzofurancarboxylic acid has a melting point of 226°–230°.

Analysis Calcd. for $C_{13}H_{11}NO_5$ (261.24): C, 59.77; H, 4.24; N, 5.36. Found: C, 59.57; H, 4.22; N, 5.51.

EXAMPLE 3

Preparation of 8-amino-1,2-dihydro-3(4H)-dibenzofurancarboxylic acid

A solution of 4.83 g. of 1,2-dihydro-8-nitro-3(4H)-dibenzofurancarboxylic acid in 150 ml. of acetic acid was reduced in the Brown hydrogenator with 1 g. of 10 percent palladium-on-charcoal catalyst. The catalyst was removed by filtration. The filtrate was evaporated, and the residue was crystallized from acetonitrile-ether to give 3.4 g. of 8-amino-1,2-dihydro- 3(4H)-dibenzofurancarboxylic acid as brown crystals, m.p. 235°–235.5° dec. This material may be used in succeeding steps without further purification. Crystallized from acetonitrileether as light brown crystals, 8-amino-1,2-dihydro-3(4H)-dibenzofurancarboxylic acid has a melting point of 231°–231.5° dec.

Analysis Calcd. for $C_{13}H_{13}NO_3$ (23/.25): C, 67.52; H, 5.67; N, 6.06. Found: C, 67.35; H, 5.68; N, 6.05.

EXAMPLE 4

Preparation of 8-amino-1,2-dihydro-3(4H)-dibenzofurancarboxylic acid ethyl ester hydrochloride A solution of 1 g. of 8-amino-1,2-dihydro-3(4H)-dibenzofurancarboxylic acid in 100 ml. of ethanol saturated with hydrogen chloride was heated at reflux temperature for 2 hours and then evaporated to dryness. The residue was crystallized from ethanol-ether to give 986 mg. (89 percent) of 8-amino-1,2-dihydro-3(4H)-dibenzofurancarboxylic acid ethyl ester hydrochloride as white crystals, m.p. 250°–251° dec. Crystallized from ethanol-ether as white crystals, 8-amino-1,2-dihydro-3(4H)-dibenzofurancarboxylic acid ethyl ester hydrochloride has a melting point of 251°–252° dec.

Analysis Calcd. for $C_{15}H_{17}NO_3 \cdot HCl$ (295.77): C, 60.91; H, 6.13; N, 4.74. Found: C, 61.11; H, 6.28; N, 4.91.

EXAMPLE 5

Preparation of 3-bromo-4-ketocyclohexanecarboxylic acid ethyl ester

A solution of 40 g. of 4-ketocyclohexanecarboxylic acid ethyl ester in 650 ml. of ether was stirred at −10° during the dropwise addition of 12.05 ml. of bromine. The resultant colorless solution was washed successively with water, saturated sodium bicarbonate solution, and again with water. The organic layer was dried over sodium sulfate and evaporated to give 59 g. of 3-bromo-4-ketocyclohexanecarboxylic acid ethyl ester as a colorless oil. This material may be used for the next step without further purification, and may be kept for 2 to 3 days under nitrogen, without significant decomposition. For analysis, a sample was distilled, b.p. 95°/0.001 mm.

Analysis Calcd. for $C_9H_{13}BrO_3$ (249.11): C, 43.39; H, 5.26. Found: C, 43.24; H, 5.22.

EXAMPLE 6

Preparation of 8-chloro-1,2-dihydro-3(4H)-dibenzofurancarboxylic acid

Method A: A suspension of 2 g. of 8-amino-1,2-dihydro-3(4H)-dibenzofurancarboxylic acid in 12 ml. of water and 20 ml. of concentrated hydrochloric acid, stirred at 0°, was treated dropwise with a cold solution of 716 mg. of sodium nitrite in 20 ml. of water. The diazotization solution was stirred at 0° for 30 minutes and then was added gradually to a cold solution of 1.3 g. of cuprous chloride in 18 ml. of concentrated hydrochloric acid. The mixture was stirred for 2.5 hours at room temperature, diluted with water, and filtered to give 1.78 g. of 8-chloro-1,2-dihydro-3(4H)-dibenzofurancarboxylic acid as tan crystals, m.p. 194°–198.5°. A pure sample of 8-chloro-1,2-dihydro-3(4H)-dibenzofurancarboxylic acid as white crystals, m.p. 198°–201°, was obtained in about 50 percent yield by sublimation at 190°/0.05 mm.

Analysis Calcd. for $C_{13}H_{11}ClO_3$ (250.68): C, 62.29; H, 4.42; N, 14.14. Found: C, 62.24; H, 4.35; N, 13.76.

Method B: A suspension of sodium 4-chlorophenoxide, prepared from 11.6 g. of 4-chlorophenol and 4.86 g. of sodium methoxide, and 22.5 g. of 3-bromo-4-ketocyclohexanecarboxylic acid ethyl ester in 300 ml. of benzene was stirred for 64 hours at room temperature. The mixture was then washed successively with 1N sodium hydroxide and water. The organic layer was dried over sodium sulfate and evaporated to give 18.30 g. of 3-(p-chlorophenoxy)-4-oxocyclohexanecarboxylic acid ethyl ester as a yellow oil. A mixture of 18.25 g. of this material and 180 g. of polyphosphoric acid was stirred for 10 minutes at room temperature and then quenched with ice and water. The resulting solution was extracted with ether. The organic layer was washed successively with 1N sodium hydroxide and water, dried and evaporated to give 15.6 g. of viscous oil, which, after distillation, gave 10.2 g. of 8-chloro-1,2-dihydro-3(4H)-dibenzofurancarboxylic acid ethyl ester as a light yellow oil, b.p. 175°–185°/1 mm. A solution of 10.2 g. of 8-chloro-1,2-dihydro-3(4H)-dibenzofurancarboxylic acid ethyl ester, 150 ml. of 1N sodium hydroxide and 300 ml. of ethanol was heated at reflux temperature for 1.5 hours and then concentrated at reduced pressure. After extraction with methylene chloride, the aqueous layer was treated with charcoal and filtered. The filtrate was cooled in ice water and acidified with 25 ml. of concentrated hydrochloric acid. The precipitate was filtered, washed with water, and dried to give 7 g. of crystals, m.p. 199.5°–201°, which were identical with the 8-chloro-1,2-dihydro-3(4H)-dibenzofurancarboxylic acid obtained by Method A.

EXAMPLE 7

Preparation of 8-fluoro-1,2-dihydro-3(4H)-dibenzofurancarboxylic acid

A suspension of sodium p-fluorophenoxide, prepared from 11.2 g. of p-fluorophenol, 5.4 g. sodium methoxide and 26.8 g. of 3-bromo-4-ketocyclohexanecarboxylic acid ethyl ester in 200 ml. of benzene was stirred for 16 hours at room temperature. The reaction mixture was washed with water, 1N sodium hydroxide, and saturated sodium chloride solution, and was dried over sodium sulfate. Evaporation of the solvent gave 22.1 g. of 3-(p-fluorophenoxy)-4-oxocyclohexanecarboxylic acid ethyl ester.

A mixture of 17.1 g. of this material and 150 g. of polyphosphoric acid was stirred for 10 minutes at room temperature, then quenched with ice water and extracted three times with ether. The organic portion was washed with sodium bicarbonate and saturated sodium chloride solutions, dried, and evaporated to dryness to give 15.8 g. of an oil which was distilled in a "Kugelrohr oven" to give 7.75 g. of 8-fluoro-1,2-dihydro-3(4H)-dibenzofurancarboxylic acid ethyl ester as a colorless oil. This material was heated at reflux temperature for 1 hour in a mixture of 75 ml. of ethanol and 50 ml. of 1N sodium hydroxide. The ethanol was evaporated under reduced pressure. After the addition of 50 ml. of water, the reaction mixture was treated with charcoal and neutralized with 25 ml. of 2N hydrochloric acid. The solids which formed were removed by filtration and crystallized from acetone-water to give 3.65 g. of 8-fluoro-1,2-dihydro-3(4H)-dibenzofurancarboxylic acid as white crystals, m.p. 208°–210°.

Analysis Calcd. for $C_{13}H_{11}FO_3$ (234.23): C, 66.66; H, 4.73. Found: C, 66.68; H, 4.93.

EXAMPLE 8

Preparation of 8-methyl-1,2-dihydro-3(4H)-dibenzofurancarboxylic acid

A suspension of sodium p-cresolate, prepared from 3.24 g. of p-cresol and 1.62 g. of sodium methoxide, and 7.45 g. of 3-bromo-4-ketocyclohexanecarboxylic acid ethyl ester in 100 ml. of dry benzene was stirred for 64 hours at room temperature. The mixture was then washed successively with water, 1N sodium hydroxide and water. The aqueous layers were extracted two times with benzene. The organic layers were dried over sodium sulfate and evaporated to give 6.11 g. of 3-(p-methylphenoxy)-4-oxocyclohexanecarboxylic acid ethyl ester as a yellow oil.

A solution of 1.9 g. of the above material in 5 ml. of ether was combined with 19 g. of polyphosphoric acid and stirred for 20 minutes at room temperature under nitrogen. The reaction was quenched by addition of ice water, and the resulting mixture was stirred until a solution was obtained. This solution was extracted three times with ether. The organic layers were washed with water, saturated sodium bicarbonate solution, water, and dried over sodium sulfate. Evaporation of the solvent gave 1.62 g. of a yellow oil which was distilled under vacuum to give 1.2 g. of 8-methyl-1,2-dihydro-3(4H)-dibenzofurancarboxylic acid ethyl ester. A solution of this material (1.2g.) in 9 ml. of 1N sodium hydroxide, and 9 ml. of ethanol was heated at reflux temperature for 1 hour under a nitrogen atmosphere. The ethanol was removed under vacuum. The residue was dissolved in water, treated with charcoal, and filtered. The filtrate was cooled in an ice water bath and acidified with 2N hydrochloric acid. The precipitate which formed was filtered and crystallized from ether-pentane to give 250 mg. of 8-methyl-1,2-dihydro-3(4H)-dibenzofurancarboxylic acid, m.p. 199°–201°.

Analysis Calcd. for $C_{14}H_{14}O_3$ (230.26): C, 73.02; H, 6.13. Found: C, 72.65; H, 6.31.

EXAMPLE 9

Preparation of 6-chloro-1,2-dihydro-3(4H)-dibenzofurancarboxylic acid

To a solution of 6.43 g. of freshly distilled 2-chlorophenol in 100 ml. of methanol was added 2.7 g. of sodium methoxide, and the resulting solution was evaporated to dryness under reduced pressure to give 7.5 g. of sodium 2-chlorophenoxide. A suspension of the above sodium salt and of 12.5 g. of 3-bromo-4-ketocyclohexanecarboxylic acid ethyl ester in 150 ml. of benzene was stirred overnight at room temperature. The reaction mixture was washed with two 50 ml. portions of water, two 50 ml. portions of 1N sodium hydroxide, and three 50 ml. portions of brine. The organic layers were dried over sodium sulfate and evaporated to dryness to give 11.85 g. of 3-(o-chlorophenoxy)-4-oxocyclohexanecarboxylic acid ethyl ester as a dark yellow oil.

A mixture of 1 g. of 3-(o-chlorophenoxy)-4-oxocyclohexanecarboxylic acid ethyl ester and 10 g. of polyphosphoric acid was stirred for 1 hour at 75°. After the addition of 25 ml. of ice water, the reaction mixture was extracted three times with 100 ml. portions of ether. The organic layers were washed with water, 1N sodium bicarbonate and with brine. The ether extracts were dried over sodium sulfate, evaporated to dryness, and the residue (955 mg.) was distilled in a Kugelrohr oven at 200°/0.2 mm. to give 475 mg. of 6-chloro-1,2-dihydro-3(4H)-dibenzofurancarboxylic acid ethyl ester as a yellow oil. A solution of this material in 10 ml. of ethanol and 5 ml. of 2N sodium hydroxide was heated at reflux temperature for 1 hour. After removal of the ethanol, the resulting cloudy solution was treated with charcoal, filtered and treated with 5 ml. of 2N HCl. The solids which formed were removed by filtration and crystallized from acetonitrile to give 250 mg. of 6-chloro-1,2-dihydro-3(4H)-dibenzofurancarboxylic acid as white crystals, m.p. 188°–192°C. Recrystallization from acetone-water gave 230 mg. of 6-chloro-1,2-dihydro-3(4H)-dibenzofurancarboxylic acid, m.p. 190°–193°C.

Analysis Calcd. for $C_{13}H_{11}ClO_3$ (250.68): C, 62.29; H, 4.42. Found: C, 61.99; H, 4.29.

EXAMPLE 10

Preparation of 7-chloro-1,2-dihydro-3(4H)-dibenzofurancarboxylic acid and 9-chloro-1,2-dihydro-3(4H)-dibenzofurancarboxylic acid Sodium 3-chlorophenoxide, prepared from 11.6 g. of 3-chlorophenol and 4.86 g. of sodium methoxide, in 300 ml. of dry benzene was stirred for 10 hours at room temperature with 21 g. of 3-bromo-4-ketocyclohexanecarboxylic acid ethyl ester. The suspension was washed twice with 100 ml. portions of water, once with 100 ml. of 1N sodium hydroxide, and thrice with 100 ml. portions of water. The aqueous layers were extracted twice with 150 ml. portions of benzene. The combined organic layers were dried with sodium sulfate and evaporated to give 20.4 g. of 3-(3-chlorophenoxy)-4-oxocyclohexanecarboxylic acid ethyl ester. A mixture of 5.63 g. of this material and 85 g. of polyphosphoric acid was stirred at 75° for 1 hour, decomposed with ice and water, and extracted three times with 250 ml. portions of ether. The organic layers were washed twice with 200 ml. portions of water, once with 150 ml. of saturated sodium bicarbonate solution, and three times with 200 ml. portions of water, and were then dried with sodium sulfate and evaporated to give 4.5 g. of brown oil. Distillation at 190°/0.2 mm. gave 3.5 g. of a mixture of the isomeric esters 7-chloro-1,2-dihydro-3(4H)-dibenzofurancarboxylic acid ethyl ester and 9-chloro-1,2-dihydro-3(4H)-dibenzofurancarboxylic acid ethyl ester. A solution of 3.48 g. of this material in 70 ml. of 1N sodium hydroxide and 140 ml. of ethanol was stirred at reflux temperature for 1 hour and then evaporated. The residue was dissolved in water, stirred with charcoal and filtered. The filtrate was acidified with concentrated hydrochloric acid, and the resulting precipitate was collected to give 2.72 g. of an isomeric mixture of 7-chloro-1,2-dihydro-3(4H)-dibenzofurancarboxylic acid and 9-chloro-1,2-dihydro-3(4H)-dibenzofurancarboxylic acid as a gray solid, m.p. 148°–163°. Recrystallization from ether-pentane gave 1.51 g. of the isomeric mixture 7-chloro-1,2-dihydro-3(4H)-dibenzofurancarboxylic acid and 9-chloro-1,2-dihydro-3(4H)-dibenzofurancarboxylic acid as yellowish crystals, m.p. 152°–180°. Crystallized from methylene chloride-ether-pentane; 7-chloro-1,2-dihydro-3(4H)-dibenzofurancarboxylic acid and 9-chloro1 1,2-dihydro-3(4H)-dibenzofurancarboxylic acid as white crystals had a melting point of 167°–185°. Analysis calc. for $C_{13}H_{11}ClO_3$ (250.68): C, 62.29; H, 4.42. Found: C, 62.38; H, 4.68.

EXAMPLE 11

Preparation of 9-chloro-1,2-dihydro-3(4H)-dibenzofurancarboxylic acid methyl ester A solution of 5.65 g. of the mixture of isomers 7-chloro-1,2-dihydro-3(4H)-dibenzofurancarboxylic acid and 9-chloro-1,2-dihydro-3(4H)-dibenzofurancarboxylic acid, m.p. 131°–155°, in 100 ml. of methanol saturated with hydrogen chloride was stirred at reflux temperature for 1 hour. Evaporation of the solvent and crystallization of the residue from ether-pentane gave 884 mg. of 9-chloro-1,2-dihydro-3(4H)-dibenzofurancarboxylic acid methyl ester as a yellowish crystals, m.p. 99°–102°. A sample for analysis was sublimed at 90°–100°/0.12 mm. as white crystals, m.p. 101°–102.5°.

Analysis Calcd. for $C_{14}H_{13}ClO_3$ (264.71): C, 63.53; H, 4.95. Found: C, 63.35; H, 4.82.

EXAMPLE 12

Preparation of 9-chloro-1,2-dihydro-3(4H)-dibenzofurancarboxylic acid

A solution of 840 mg. of 9-chloro-1,2-dihydro-3(4H)-dibenzofurancarboxylic acid methyl ester in 15 ml. of 1N sodium hydroxide and 30 ml. of ethanol was stirred at reflux temperature for 1 hour and then evaporated. The residue was dissolved in water and extracted three times with 75 ml. portions of methylene chloride. The aqueous layer was stirred with charcoal, and filtered, and the filtrate was acidified with concentrated hydrochloric acid. The precipitate was filtered, dried and crystallized from tetrahydrofuran-ether-pentane to give 452 mg. of 9-chloro-1,2-dihydro-3(4H)-dibenzofurancarboxylic acid as white crystals, m.p. 189°–190°.

Analysis Calcd. for $C_{13}H_{11}ClO_3$ (250.68): C, 62.29; H, 4.42. Found: C, 62.51; H, 4.51.

EXAMPLE 13

Preparation of 7-acetamido-1,2-dihydro-3(4H)-dibenzofurancarboxylic acid ethyl ester A suspension of 15.1 g. of 3-acetamidophenol and 13.8 g. of potassium carbonate in 60 ml. of dimethylformamide was heated with stirring at 100° for 10 minutes. A solution of 24.9 g. of 3-bromo-4-ketocyclohexanecarboxylic acid ethyl ester in 25 ml. of dimethylformamide was added dropwise to the above suspension. After 15 minutes, the reaction mixture was concentrated, diluted with water and extracted three times with ether. The ether extracts were washed with 1N sodium hydroxide, water, and dried over sodium sulfate. Evaporation of the solvent gave 18.0 g. of 3-(m-acetamidophenoxy)-4-oxocyclohexanecarboxylic acid ethyl ester. A mixture of 16 g. of this material and 160 g. of polyphosphoric acid was stirred for 30 minutes at room temperature. An excess of ice water was added. The precipitate which formed was filtered, dried, dissolved in methylene chloride, and filtered through a column of alumina (activity grade II). The methylene chloride eluates were evaporated to give 11.1 g. of an oil which was crystallized from methylene chloride-ether-pentane to give 4.5 g. of 7-acetamido-1,2-dihydro-3(4H)-dibenzofurancarboxylic acid ethyl ester, m.p. 115°–116°.

Analysis Calcd. for $C_{17}H_{19}NO_4$ (301.33): C, 67.76; H, 6.36; N, 4.65. Found: C, 68.07; H, 6.35; N, 4.62.

EXAMPLE 14

Preparation of 7-amino-1,2-dihydro-3(4H)-dibenzofurancarboxylic acid ethyl ester hydrochloride A solution of 2.9 g. of 7-acetamido-1,2-dihydro-3(4H)-dibenzofurancarboxylic acid ethyl ester in ethanolic hydrogen chloride was heated at reflux temperature for 2 hours. The solvent was removed under vacuum. Crystallization of the residue from ethanol-ether gave 2.2 g. of 7-amino-1,2-dihydro-3(4H)-dibenzofurancarboxylic acid ethyl ester hydrochloride, m.p. 226°–228°.

Analysis Calcd. for $C_{15}H_{17}NO_3 \cdot HCl$ (295.75): C, 60.91; H, 6.13; N, 4.74. Found: C, 60.62; H, 6.24; N, 4.64.

EXAMPLE 15

Preparation of 7-chloro-1,2-dihydro-3(4H)-dibenzofurancarboxylic acid

A solution of 145 mg. of sodium nitrite in 2 ml. of water was added dropwise, under nitrogen, to a cooled solution of 590 mg. of 7-amino-1,2-dihydro-3(4H)-dibenzofurancarboxylic acid ethyl ester hydrochloride in 5 ml. of acetic acid:water (1:1). The resulting solution was added dropwise, under nitrogen, to a suspension of 238 mg. of cuprous chloride in 2 ml. of conc. hydrochloric acid at 5°. The reaction mixture was stirred at room temperature for 30 minutes, then extracted three times with ether. The ether layers were washed with 1N hydrochloric acid, 1N sodium hydroxide, water, and dried over sodium sulfate. Evaporation of the solvent gave 510 mg. of an oil, which was distilled in a Kugelrohr oven, to give 444 mg. of 7-chloro-1,2-dihydro-3(4H)-dibenzofurancarboxylic acid ethyl ester as a yellow oil. A solution of 420 mg. of this material, 5 ml. of 1N sodium hydroxide, and 10 ml. of ethanol was heated at reflux temperature for 1 hour. The solvent was removed under vacuum. The remaining residue was dissolved in water. The aqueous solution was extracted two times with ether, cooled and acidified with 2N hydrochloric acid. The precipitate which formed was filtered and crystallized from acetone-water to give 290 mg. of a solid, m.p. 189°–191°. This material was recrystallized from acetone-ether to give 110 mg. of 7-chloro-1,2-dihydro-3(4H)-dibenzofurancarboxylic acid, m.p. 194°–196°.

Analysis Calcd. for $C_{13}H_{11}ClO_3$ (250.68): C, 62.29; H, 4.42. Found: C, 62.33; H, 4.22.

EXAMPLE 16

Preparation of 7-acetamido-1,2-dihydro-3(4H)-dibenzofurancarboxylic acid

A solution of 1,2 g. of 7-acetamido-1,2-dihydro-3(4H)-dibenzofurancarboxylic acid ethyl ester, 10 ml. of 1N sodium hydroxide, and 10 ml. of ethanol was heated at reflux temperature for 1 hour. The solvent was removed under vacuum. The residue was dissolved in water and acidified with 2N hydrochloric acid. The precipitate was filtered and crystallized from acetone-water to give 75 mg. of 7-acetamido-1,2-dihydro-3(4H)-dibenzofurancarboxylic acid, m.p. 229°–230°.

Analysis Calcd. for $C_{15}H_{15}NO_4$ (273.28): C, 65.92; H, 5.53; N, 5.13. Found: C, 65.71; H, 5.26; N, 4.98.

EXAMPLE 17

Preparation of 7-amino-1,2-dihydro-3(4H)-dibenzofurancarboxylic acid hydrochloride A solution of 100 mg. of 7-amino-1,2-dihydro-3(4H)-dibenzofurancarboxylic acid ethyl ester hydrochloride, 3 ml. of 1N sodium hydroxide and 10 ml. of ethanol was heated at reflux temperature for 1 hour. The solvent was removed under vacuum. The residue was dissolved in water, cooled, and acidified with 1N hydrochloric acid. The solid was filtered and crystallized from methanol/ether to give 45 mg. of 7-amino-1,2-dihydro-3(4H)-dibenzofurancarboxylic acid hydrochloride, m.p. 290°–300°.

Analysis Calcd. for $C_{13}H_{13}NO_3 \cdot HCl$ (267.70): C, 58.33; H, 5.27; N, 5.23; Cl, 13.24. Found: C, 58.32; H, 5.48; N, 5.14; Cl, 13.37.

EXAMPLE 18

Preparation of 7-methoxy-1,2-dihydro-3(4H)-dibenzofurancarboxylic acid

A suspension of 6.2 g. of freshly distilled 3-methoxyphenol and 6.9 g. of potassium carbonate in 20 ml. of dimethylformamide was heated at 100° for 15 minutes. To the stirred suspension was added dropwise 12.5 g. of 3-bromo-4-ketocyclohexanecarboxylic acid ethyl ester in 5 ml. of dimethylformamide, and the resulting mixture was stirred at 100° for 30 minutes. After cooling, 150 ml. of water was added, and the reaction mixture was extracted with three 150 ml. portions of ether. The ether layers were washed with 1N sodium hydroxide and water, dried over sodium sulfate, and treated with charcoal. Evaporation of the solvent gave 8.5 g. of 3-(m-methoxyphenoxy)-4-oxocyclohexanecarboxylic acid ethyl ester as a yellow oil. A mixture of this material and 85 g. of polyphosphoric acid was stirred for 15 minutes at room temperature, and added to 150 ml. of ice water. Thereafter, the mixture was extracted with three 150 ml. portions of ether. The ether extracts were washed with saturated aqueous sodium bicarbonate and brine, and dried over sodium sulfate. Evaporation of the solvent gave 7 g. of 7-methoxy-1,2-dihydro-3(4H)-dibenzofurancarboxylic acid ethyl ester as a dark oil, which was dissolved in 100 ml. of ethanol and 50 ml. of 2N sodium hydroxide. The resulting solution was heated at reflux temperature for 1 hour. The ethanol was removed under reduced pressure. After the addition of 150 ml. of water, the reaction mixture was extracted with ether. The aqueous layer was treated with charcoal, cooled in an ice water bath, and neutralized with 50 ml. of 2N hydrochloric acid. The solids which formed were removed by filtration and were crystallized from acetone-water to give 3.8 g. of crystals, m.p. 175°–180°. Recrystallization from acetonitrile-water gave 7-methoxy-1,2-dihydro-3(4H)-dibenzofurancarboxylic acid as white crystals, m.p. 181°–183°.

Analysis Calcd. for $C_{14}H_{14}O_4$ (246.25): C, 68.28; H, 5.73. Found: C, 68.45; H, 5.91.

EXAMPLE 10

Preparation of 7,9-dimethoxy-1,2-dihydro-3(4H)-dibenzofurancarboxylic acid

A suspension of 3.08 g. of 3,5-dimethoxyphenol, 2.76 g. of potassium carbonate and 4.98 g. of 3-bromo-4-ketocyclohexanecarboxylic acid ethyl ester in 30 ml. of dimethylformamide was stirred at 100° for 2 hours. Thereafter, 150 ml. of ice water was added, and the resulting solution was extracted three times with 100 ml. portions of ether. The ether layers were washed with 1N sodium hydroxide and with water, dried over sodium sulfate, and evaporated to dryness. The residue (3.3 g.) 3-(3,5dimethoxyphenoxy)-4-oxocyclohexanecarboxylic acid ethyl ester was stirred at room temperature for 15 minutes with 33 g. of polyphosphoric acid. After the addition of 150 ml. of water, the reaction mixture was extracted three times with 100 ml. portions of ether. The ether layers were washed with sodium bicarbonate and saturated sodium chloride solutions, dried over sodium sulfate, and evaporated to dryness to give 2.7 g. of 7,9-dimethoxy-1,2-dihydro-3(4H)-dibenzofurancarboxylic acid ethyl ester. This material was dissolved in 50 ml. of ethanol and 25 ml. of 2N sodium hydroxide, and the resulting solution was heated at reflux temperature for 1 hour. The reaction mixture was cooled, and the ethanol was removed under reduced pressure. The residue which formed was diluted with water, treated with charcoal, cooled in an ice bath and neutralized with 25 ml. of 2N hydrochloric acid. The solids which formed were removed by filtration and crystallized from acetone-water to give 1 g. of 7,9-dimethoxy-1,2-dihydro-3(4H)-dibenzofurancarboxylic acid, m.p. 194°–196°.

Analysis Calcd. for $C_{15}H_{16}O_5$ (276.29): C, 65.21; H, 5.84. Found: C, 65.13; H, 5.95.

EXAMPLE 20

Preparation of 7,9-dichloro-1,2-dihydro-3(4H)-dibenzofurancarboxylic acid

A solution of 3.12 g. of 3-bromo-4-ketocyclohexanecarboxylic acid ethyl water in 5 ml. of dimethylformamide was added dropwise to a suspension of 2.04 g. of 3,5-dichlorophenol and 0.865 g. of potassium carbonate in 25 ml. of dimethylformamide. The resulting mixture was heated for 2 hours at 100°. Thereafter, it was cooled to room temperature, diluted with water, and extracted three times with ether. The organic layers were washed with water, saturated sodium bicarbonate solution, and water, dried over sodium sulfate, and evaporated to give 3.7 g. of 3-(3,5-dichlorophenoxy)-4-oxocyclohexanecarboxylic acid ethyl ester. This material was combined with 38 g. of polyphosphoric acid and heated for 1 hour at 70°. The reaction was quenched by addition of ice water, and the resulting solution was extracted three times with ether. The organic layers were washed with water, saturated sodium bicarbonate solution, and water, dried over sodium sulfate, and evaporated to give 2.7 g. of 7,9-dichloro-1,2-dihydro-3(4H)-dibenzofurancarboxylic acid ethyl ester. A solution of 2.7 g. of 7,9-dichloro-1,2-dihydro-3(4H)-dibenzofurancarboxylic acid ethyl ester, 25 ml. of 1N sodium hydroxide, and 25 ml. of ethanol was heated at reflux temperature for 1 hour. The ethanol was removed under vacuum. The residue was dissolved in water, extracted two times with ether, cooled in an ice water bath, and acidified with 2N hydrochloric acid. The precipitate which formed was filtered and dried under vacuum to give 2.0 g. of a solid, m.p. 190°–200°. Crystallization from acetone-ether gave 1.06 g. of 7,9-dichloro-1,2-dihydro-3(4H)-dibenzofurancarboxylic acid, m.p. 223°–225°.

Analysis Calcd. for $C_{13}H_{10}Cl_2O_3$ (285.13): C, 54.76; H, 3.54. Found: C, 54.65; H, 3.86.

EXAMPLE 21

Preparation of 3-(4-cyanophenoxyimino)cyclohexanecarboxylic acid

To a solution of 2.26 g. of potassium t-butoxide in 18 ml. of dimethylsulfoxide, stirred vigorously at room temperature, was added 1.57 g. of 3-oxyiminocyclohexanecarboxylic acid. After 15 minutes, the mixture was treated with 1.21 g. of p-fluorobenzonitrile, stirred for 2 hours, diluted with 150 ml. of saturated sodium chloride solution, and acidified with acetic acid. The solid which formed was removed by filtration, dried and crystallized from tetrahydrofuran-ether-pentane to give 1.6 g. of 3-(4-cyanophenoxyimino)cyclohexanecarboxylic acid as white crystals, m.p. 153°–154°.

Analysis Calcd. for $C_{14}H_{14}N_2O_3$ (258.28): C, 65.10; H, 5.46; N, 10.85. Found: C, 65.01; H, 5.48; N, 10.87.

EXAMPLE 22

Preparation of 8-cyano-1,2-dihydro-3(4H)-dibenzofurancarboxylc acid

A solution of 258 mg. of 3-(4-cyanophenoxyimino)-cyclohexanecarboxylic acid in 25 ml. of acetic acid saturated with hydrogen chloride was heated on a steambath overnight, and then evaporated to dryness. The residue was digested on the steambath with 3 ml. of acetic acid. Thereafter, the mixture cooled to 25°, and the solid which formed was removed by filtration to give 99 mg. of 8-cyano-1,2-dihydro-3(4H)-dibenzofurancarboxylic acid as white crystals, m.p. 253°–255°. Crystallized from tetrahydrofuran-ether-pentane, as white crystals, 8-cyano-1,2-dihydro-3(4H)-dibenzofurancarboxylic acid had a melting point of 249°–250°.

Analysis Calcd. for $C_{14}H_{11}NO_3$ (241.26): C, 69.70; H, 4.59; N, 5.80. Found: C, 69.69; H, 4.60; N, 5.77.

EXAMPLE 23

Preparation of 8-cyano-3,4-dihydro-1(2H)-dibenzofurancarboxylic acid

Fractional crystallization of 15 g. of the mother liquors obtained from the preparation of 8-cyano-1,2-dihydro-3(4H)-dibenzofurancarboxylic acid gave 4.5 g. of a tan solid, m.p. 185°–190°. Two g. of this material was filtered through a column of 8 g. of Florisil. The column was eluted successively with benzene, methylene chloride, ether and ethyl acetate. The methylene chloride and the ether eluates were combined and crystallized twice from methylene chloride-ether-pentane to give 340 mg. of 8-cyano-3,4-dihydro-1(2H)-dibenzofurancarboxylic acid, m.p. 195°–196°.

Analysis Calcd. for $C_{14}H_{11}NO_3$ (241.26): C, 69.70; H, 4.59; N, 5.80. Found: C, 69.75; H, 4.73; N, 5.81.

EXAMPLE 24

Preparation of 8-carbamoyl-1,2-dihydro-3(4H)-dibenzofurancarboxylic acid ethyl ester A suspension of 1 g. of 8-cyano-1,2-dihydro-3(4H)-dibenzofurancarboxylic acid in 100 ml. of ethanol was stirred in an ice water bath and was saturated with hydrogen chloride. The mixture was refrigerated overnight and then heated to reflux temperature for 4 hours with the introduction of hydrogen chloride. The solution was evaporated to dryness, and the residue was partitioned between methylene chloride and dilute sodium hydroxide. The organic layer was washed with water, dried and evaporated to give 1.1 g. of solid, which was crystallized from methylene chloride-ether to give 283 mg. of 8-carbamoyl-1,2-dihydro-3(4H)-dibenzofurancarboxylic acid ethyl ester as white crystals, m.p. 206.5°–207.5°. Crystallized twice from methylene chloride-ether as white crystals, 8-carbamoyl-1,2-dihydro-3(4H)-dibenzofurancarboxylic acid ethyl ester had a melting point of 207.5°–208°.

Analysis Calcd. for $C_{16}H_{17}NO_4$ (287.33): C, 66.88; H, 5.97; N, 4.87. Found: C, 67.01; H, 5.69; N, 4.85.

EXAMPLE 25

Preparation of 1,2-dihydro-3(4H),8-dibenzofurandicarboxylic acid

A mixture of 250 mg. of 8-cyano-1,2-dihydro-3(4H)-dibenzofurancarboxylic acid and 3 ml. of a 30 percent solution of potassium hydroxide in water was heated for 3 hours at 100°. The solution thus obtained was diluted with water, cooled in an ice water bath, and acidified with 2N hydrochloric acid. The precipitate which formed was filtered and dried under vacuum. The solid obtained was crystallized from methanol to give 75 mg. of 1,2-dihydro-3(4H),8-dibenzofurandicarboxylic acid, m.p. 322°–323°. An additional 130 mg. of product, m.p. 321°–322°, was obtained from the mother liquors.

Analysis Calcd. for $C_{14}H_{12}O_5$ (260.24): C, 64.61; H, 4.65. Found: C, 64.39; H, 5.01.

EXAMPLE 26

Preparation of 8-cyano-3,4-dihydro-2(1H)-dibenzofurancarboxylic acid

To a solution of 1.47 g. of potassium t-butoxide in 11 ml. of dimethylsulfoxide stirred vigorously at room temperature, was added 993 mg. of 4-oxyiminocyclohexanecarboxylic acid. After 20 minutes, the reaction mixture was treated with 754 mg. of 4-fluorobenzonitrile, stirred for 2 hours, diluted with 100 ml. of saturated sodium chloride solution and acidified with acetic acid. Precipitate was removed by filtration, washed with water and with pentane and dried to give 670 mg. of 4-(4-cyanophenoxyimino)-cyclohexanecarboxylic acid as a tan powder, m.p. 160°–161° dec. This material can be used in the succeeding step without further purification.

A solution of 570 mg. of 4-(4-cyanophenoxyimino) cyclohexanecarboxylic acid in 10 ml. of acetic acid saturated with hydrogen chloride was heated on a steambath for 15 hours. The reaction mixture was cooled to about 25°, and the solid which formed was removed by filtration. Crystallization from tetrahydrofuran-ether gave 230 mg. of 8-cyano-3,4-dihydro-2(1H)-dibenzofurancarboxylic acid as white crystals, m.p. 251°–251.5°. Recrystallized from tetrahydrofuranether as white crystals, 8-cyano-3,4-dihydro-2-(1H)-dibenzofurancarboxylic acid had a melting point of 249.5°–250.5°.

Analysis Calcd. for $C_{14}H_{11}NO_3$ (241.26): C, 69.70; H, 4.59; N, 5.80. Found: C, 69.85; H, 4.72; N, 5.81.

EXAMPLE 27

Preparation of 8-acetyl-1,2-dihydro-3(4H)-dibenzofurancarboxylic acid

To a solution of 9 g. of potassium t-butoxide in 50 ml. of dimethylsulfoxide, stirred vigorously at room temperature under a nitrogen atmosphere, was added 6.3 g. of 3-oxyiminocyclohexanecarboxylic acid. After 30 minutes, the mixture was treated with 4.86 ml. of 4-fluoroacetophenone, stirred for 3.5 hours, diluted with 0.5 liter of saturated sodium chloride solution, and acidified with acetic acid. The solid was removed by filtration, washed with water and with pentane, dried and digested with 400 ml. of boiling tetrahydrofuran. Insoluble inorganic material which formed was removed by filtration, and the filtrate was evaporated to dryness. The residue was crystallized from methanol-ether to give 2.1 g. of 3-(4-acetylphenoxyimino)-cyclohexanecarboxylic acid as light brown crystals, m.p. 167°–168.5° dec. A solution of 1.9 g. of this material in 25 ml. of acetic acid saturated with hydrogen chloride was heated on a steambath for 15 hours. The reaction mixture was cooled to about 25°, and the solid which formed was removed by filtration. Crystallization from tetrahydrofuran-ether gave 522 mg. of 8-acetyl-1,2-dihydro-3(4H)-dibenzofurancarboxylic acid as grayish crystals, m.p. 234°–235°. Recrystallized from tetrahydrofuranether as white crystals, 8-acetyl-1,2-dihydro-3(4H)-dibenzofurancarboxylic acid had a melting point of 234°–235°.

Analysis Calcd. for $C_{15}H_{14}O_4$ (258.28): C, 69.75; H, 5.46. Found: C, 69.72; H, 5.61.

EXAMPLE 28

Preparation of 8-chloro-1,2,3,4-tetrahydrodibenzothiophene-3-carboxylic acid ether ester A solution of 59 g. of 3-bromo-4-ketocyclohexanecarboxylic acid ethyl ester in 250 ml. of ethanol was added at reflux temperature over a one-hour period to a stirred solution of 34 g. of 4-chlorobenzenthiol and 15.2 g. of potassium hydroxide in 750 ml. of ethanol. The reaction mixture was heated for another hour, cooled and filtered. The filtrate was evaporated, and the residue partitioned between ether and water. The ether layer was dried, evaporated, and the residue (75 g.) was distilled to give 55 g. of 3-(4-chloro-phenylthio)-4-oxo-cyclohexanecarboxylic acid ethyl ester as a light yellow oil, b.p. 190°10.04 mm. The product solidified on standing, pale yellow crystals, m.p. 63°–72°. The mixture of 25 g. of this material and 375 g. of polyphosphoric acid was stirred at 80°–85° for 3 decomposed with ice and water, and extracted with ether. The ether solution was washed successively with saturated sodium bicarbonate solution and water, dried with sodium sulfate, and evaporated to give 23 g. of 8-chloro-1,2,3,4-tetrahydrodibenzothiophene-3-carboxylic acid ethyl ester, yellow oil which gradually crystallized, m.p. 60°–66°. This material may be used in the next step without further purification. Recrystallized from hexane as white crystals, 8-chloro-1,2,3,4-tetrahydrodibenzothiophene-3-carboxylic acid ethyl ester had a melting point of 75°–77°.

Analysis Calcd. for $C_{15}H_{15}ClO_2S$ (294.80): C, 61.12; H, 5.13. Found: C, 61.14; H, 5.13.

EXAMPLE 29

Preparation of 8-chloro-1,2,3,4-tetrahydrodibenzothiophene-3-carboxylic acid

A solution of 22.8 g. of 8-chloro-1,2,3,4-tetrahydrodibenzothiophene-3-carboxylic acid ethyl ester, 320 ml. of 1N sodium hydroxide, and 640 ml. of ethanol were stirred at reflux temperature for 5 hours and then concentrated to a small volume. The residue was mixed with 0.5 liter of water, charcoal, and thereafter filtered. The filtrate was cooled while adding 50 ml. of concentrated hydrochloric acid. The resultant precipitate was removed by filtration and dried to give 19.1 g. of a solid, m.p. 222°–229°. Crystallization from acetone-ether gave 10.75 g. of 8-chloro-1,2,3,4-tetrahydrodibenzothiophene-3-carboxylic acid as yellow crystals, m.p. 228°–231°.

Analysis Calcd. for $C_{13}H_{11}ClO_2S$ (266.74): C, 58.54; H, 4.16. Found: C, 58.65; H, 4.31.

EXAMPLE 30

Preparation of 1,2-dihydro-3(4H),8-dibenzofurandicarboxylic acid diethyl ester

A solution of 226 mg. of 1,2-dihydro-3(4H),8-dibenzofurandicarboxylic acid in 50 ml. of ethanol saturated with hydrogen chloride was heated at reflux temperature for one hour while continuing introduction of hydrogen chloride. Gas introduction was terminated, and the solution was boiled for an additional two hours and then evaporated. The oily residue was dissolved in 75 ml. of methylene chloride and the solution was washed with one 25 ml. portion of 1N sodium hydroxide and two 25 ml. portions of water. The aqueous layers were extracted with two 50 ml. portions of methylene chloride. The organic layers were combined, dried with anhydrous sodium sulfate and evaporated to dryness to give 247 mg. of oil which crystallized, m.p. 58°–61°. Recrystallization from ether-pentane afforded 179 mg. of 1,2-dihydro-3(4H),8-dibenzofurandicarboxylic acid diethyl ester, m.p. 63°–63.5°.

Analysis Calcd. for: $C_{18}H_{20}O_5$ (316.34): C, 68.34; H, 6.37. Found: C, 68.49; H, 6.54.

EXAMPLE 31

Preparation of 7-chloro-1,2-dihydro-3-(4H)-dibenzofurancarboxylic acid 2-dimethylaminoethyl ester hydrochloride A mixture of 251 mg. of 7-chloro-1,2-dihydro-3(4H)-dibenzofurancarboxylic acid, 304 mg. of anhydrous potassium carbonate and 25 ml. of dimethylformamide was stirred at room temperature for 0.75 hour. A solution of 173 mg. of 2-dimethylaminoethyl chloride hydrochloride in 5 ml. of dimethylformamide was then added and the mixture was stirred for 16 hours, heated at reflux temperature for one hour and evaporated. The residue was dissolved in 100 ml. of methylene chloride and washed with three 50 ml. portions of water. The aqueous layers were extracted with two 100 ml. portions of methylene chloride. The organic layers were combined, dried with anhydrous sodium sulfate and evaporated. A solution of the residual oil in methanol was acidified with methanolic hydrogen chloride and evaporated. Crystallization of the residue from methylene chloride-ether containing a little methanol yielded 174 mg. of 7-chloro-1,2-dihydro-3(4H)-dibenzofurancarboxylic acid 2-dimethylaminoethyl ester hydrochloride, m.p. 178.5°–181°.

Analysis Calcd. for: $C_{17}H_{20}ClNO_3 \cdot HCl$ (358.27):
C, 56.99; H, 5.91; N 3.91.
Found: C, 56.74; H, 5.89; N, 3.87.

EXAMPLE 32

Preparation of
2,3-dihydro-7-nitro-1H-cyclopenta[b]benzofuran-1-carboxylic acid and
1,3-dihydro-7-nitro-2H-cyclopenta[b]benzofuran-2-carboxylic acid A mixture of 5.5 g. of potassium t-butoxide and 3.5 g. of 3-oxyiminocyclopentanecarboxylic acid in 45 ml. of dimethylsulfoxide was treated with 2.6 ml. of 4-fluoronitrobenzene, stirred at room temperature for 1.5 hours, diluted with 475 ml. of saturated sodium chloride solution and acidified with acetic acid. The precipitate which formed was removed by filtration, washed successively with water and pentane, dried and crystallized from tetrahydrofuran-ether-pentane to give 811 mg. of yellow crystals, m.p. 141.5°–142.5°. 291 mg. of the product so obtained was treated with 3.5 ml. of a saturated solution of hydrogen chloride in acetic acid, and the mixture was stirred for 17 hours at room temperature. The solid was removed by filtration, washed with acetic acid and dried to give 201 mg. of white crystals, m.p. 203°–205° (dec.). The product was shown by NMR spectra to contain a 7:3 ratio of 2,3-dihydro-7-nitro-1H-cyclopenta[b]benzofuran-1-carboxylic acid and 1,3-dihydro-7-nitro-2H-cyclopenta[b]benzofuran-2-carboxylic acid.

2,3-Dihydro-7-nitro-1H-cyclopenta[b]benzofuran-1-carboxylic acid or 1,3-dihydro-7-nitro-2H-cyclopenta[b]benzofuran-2-carboxylic acid can be converted to 2,3-dihydro-7-amino-1H-cyclopenta[b]benzofuran-1-carboxylic acid or 1,3-dihydro-7-amino-2H-cyclopenta[b]benzofuran-2-carboxylic acid, respectively, utilizing known procedures, for example, by chemical reduction, for instance, with iron and hydrochloric acid, or by catalytic reduction employing a catalyst, such as Raney nickel and the like.

2,3-Dihydro-7-amino-1H-cyclopenta[b]benzofuran-1-carboxylic acid or 1,3-dihydro-7-amino-2H-cyclopenta[b]benzofuran-2-carboxylic acid can be converted to 2,3-dihydro-7-acylamido-1H-cyclopenta[b]benzofuran-1-carboxylic acid or 1,3-dihydro-7-acylamido-2H-cyclopenta[b]benzofuran-2-carboxylic acid, respectively, utilizing known procedures, for example, acylation with an acylating agent, such as acyl halide or an acyl anhydride.

2,3-Dihydro-7-amino-1H-cyclopenta[b]benzofuran-1-carboxylic acid or 1,3-dihydro-7-amino-2H-cyclopenta[b]benzofuran-2-carboxylic acid can be converted to 2,3-dihydro-7-mono-lower alkylamino-1H-cyclopenta[b]benzofuran-1-carboxylic acid (or 2,3-dihydro-7-di-lower-alkylamino-1H-cyclopenta[b]benzofuran-1-carboxylic acid) or 1,3-dihydro-7-mono-lower alkylamino-2H-cyclopenta[b]benzofuran-2-carboxylic acid (or 1,3-dihydro-7-di-lower-alkylamino-2H-cyclopenta[b]benzofuran-2-carboxylic acid), respectively, utilizing known procedures, for example, utilizing an alkylating agent, such as an alkyl halide.

2,3-Dihydro-7-amino-1H-cyclopenta[b]benzofuran-1-carboxylic acid or 1,3-dihydro-7-amino-2H-cyclopenta[b]benzofuran-2-carboxylic acid can be converted to a diazonium salt utilizing known procedures, for example, by reaction with sodium nitrite and a mineral acid, such as hydrohalic acid. The diazonium group can then be replaced by halogen, cyano, hydroxy, lower alkoxy or hydrogen, utilizing known procedures, for example, by mixing a diazonium salt solution with, for example, a cuprous halide, cuprous cyanide, water, an alcohol or a reducing agent, such as hypophosphoric acid, respectively, at room temperature or occasionally at elevated temperature to obtain the corresponding 2,3-dihydro-7-halo-1H-cyclopenta[b]benzofuran-1-carboxylic acid or 1,3-dihydro-7-halo-2H-cyclopenta[b]benzofuran-2-carboxylic acid, respectively, or the corresponding 2,3-dihydro-7-hydroxy-1H-cyclopenta[b]benzofuran-1-carboxylic acid or 1,3-dihydro-7-hydroxy-2H-cyclopenta[b]benzofuran-2-carboxylic acid, respectively, or the corresponding 2,3-dihydro-7-lower alkoxy-1H-cyclopenta[b]benzofuran-1-carboxylic acid or 1,3-dihydro-7-lower alkoxy-2H-cyclopenta[b]benzofuran-2-carboxylic acid, respectively, or the corresponding 2,3-dihydro-1H-cyclopenta[b]benzofuran-1-carboxylic acid or 1,2-dihydro-2H-cyclopenta[b]benzofuran-2-carboxylic acid, respectively.

EXAMPLE 33

Preparation of
3-(4-cyanophenoxyimino)cyclopentanecarboxylic acid

A mixture of 5.5 g. of potassium t-butoxide and 3.65 g. of 3-oxyiminocyclopentanecarboxylic acid in 40 ml. of dimethylsulfoxide was treated with 2.96 g. of 4-fluorobenzonitrile, stirred at room temperature for 3 hours, diluted with 400 ml. of saturated sodium chloride solution and acidifed with 25 ml. of acetic acid. The precipitate which formed was removed by filtration, washed successively with water and pentane, dried and crystallized from tetrahydrofuran-ether-pentane to give 2.5 g. of 3-(4-cyanophenoxyimino)cyclopentanecarboxylic acid, tan crystals, m.p. 160.5°–161° (dec.)

Analysis Calcd. for $C_{13}H_{12}N_2O_3$ (244.24):
C, 63.92; H, 4.95; N, 11.47.
Found: C, 63.70; H, 5.02; N, 11.36.

EXAMPLE 34

Preparation of
7-cyano-2,3-dihydro-1H-cyclopenta[b]benzofuran-1-carboxylic acid and
7-cyano-1,3-dihydro-2H-cyclopenta[b]benzofuran-2-carboxylic acid.

A mixture of 1.06 g. of 3-(4-cyanophenoxyimino)cyclopentanecarboxylic acid and 5 ml. of a saturated solution of hydrogen chloride in acetic acid was stirred for 21 hours at room temperature. The solid was removed by filtration, washed with hexane-acetic acid (2:1) and then with hexane and dried to give 1.05 g. of a tan powder, m.p. 206°–208° (dec.). The product was shown by NMR spectra to be a mixture containing an approximately 1:1 ratio of 7-cyano-2,3-dihydro-1H- cyclopenta[b]benzofuran-1-carboxylic acid and 7-cyano-1,3-dihydro-2H-cyclopenta[b]benzofuran-2-carboxylic acid.

7-Cyano-2,3-dihydro-1H-cyclopenta[b]benzofuran-1-carboxylic acid or 7-cyano-1,3-dihydro-2H-cyclopenta[b]benzofuran-2-carboxylic acid can be converted to 7-carboxy-2,3-dihydro-1H-cyclopenta[b]benzofuran-1-carboxylic acid or 7-carboxy-1,3-dihydro-2H-cyclopenta[b]benzofuran-2-carboxylic acid, respectively, utilizing known procedures, for example, hydrolysis with acid or base in water or alcohol.

7-Cyano-2,3-dihydro-1H-cyclopenta[b]benzofuran-1-carboxylic acid or 7-cyano-1,3-dihydro-2H-cyclopenta[b]benzofuran-2-carboxylic acid can be converted to the 7-amido-2,3-dihydro-1H-cyclopenta[b]benzofuran-1-carboxylic acid or 7-amido-1,3-dihydro-2H-cyclopenta[b]benzofuran-2-carboxylic acid, respectively, utilizing known procedures, for example, partial hydrolysis, in strong hydrochloric acid or polyphosphoric acid.

7-Cyano-2,3-dihydro-1H-cyclopenta[b]benzofuran-1-carboxylic acid or 7-cyano-1,3-dihydro-2H-cyclopenta[b]benzofuran-2-carboxylic acid can be converted to a 7-lower alkanoyl-2,3-dihydro-1H-cyclopenta[b]benzofuran-1-carboxylic acid or a 7-lower alkanoyl-1,3-dihydro-2H-cyclopenta[b]benzofuran-2-carboxylic acid, respectively, utilizing known procedures, for example, a Grignard reagent, such as a lower alkyl magnesium halide.

EXAMPLE 35

Capsule Formulation

| | Per Capsule |
|---|---|
| 8-Cyano-1,2-dihydro-3(4H)-dibenzofurancarboxylic acid | 50 mg |
| Lactose, U.S.P. | 125 mg |
| Corn Starch, U.S.P. | 30 mg |
| Talc, U.S.P. | 5 mg |
| Total Weight | 210 mg |

Procedure
1. 50 Parts of 8-cyano-1,2-dihydro-3(4H)-dibenzofurancarboxylic acid is mixed with 125 parts of lactose and 30 parts of corn starch in a suitable mixer.
2. The mixture is further blended by passing through a Fitzpatrick Comminuting Machine with a No. 1A screen with knives forward.
3. The blended powder is returned to the mixer, 5 parts talc are added and blended thoroughly.
4. The mixture is filled into No. 4 hard shell gelatin capsules on a Parke Davis capsulating machine.

EXAMPLE 36

Tablet Formulation

| | Per Tablet |
|---|---|
| 8-Cyano-1,2-dihydro-3(4H)-dibenzofurancarboxylic acid | 25 mg |
| Dicalcium Phosphate Dihydrate, Unmilled | 175 mg |
| Corn Starch | 24 mg |
| Magnesium Stearate | 1 mg |
| Total Weight | 225 mg |

Procedure:
1. 25 Parts of 8-cyano-1,2-dihydro-3(4H)-dibenzofurancarboxylic acid and 24 parts of corn starch are mixed together and passed through a No. 00 screen in Model "J" Fitzmill with hammers forward.
2. This premix is then mixed with 175 parts of dicalcium phosphate and one-half of a part of the magnesium stearate, and passed through a No. 1A screen in Model "J" Fitzmill with knives forward, and slugged.
3. The slugs are passed through a No. 2A plate in a Model "D" Fitzmill at slow speed knives forward, and the other one-half of a part magnesium stearate is added.
4. The mixture is mixed and compressed.

EXAMPLE 37

Tablet Formulation

| | Per Tablet |
|---|---|
| 8-Cyano-1,2-dihydro-3(4H)-dibenzofurancarboxylic acid | 100 mg |
| Lactose, U.S.P | 202 mg |
| Corn Starch, U.S.P. | 80 mg |
| Amijel BO11* | 20 mg |
| Calcium Stearate | 8 mg |
| Total Weight | 410 mg |

*A prehydrolyzed food grade corn starch. Any similar prehydrolyzed corn starch may be used.

Procedure:
1. 100 Parts of 8-cyano-1,2-dihydro-3(4H)-dibenzofurancarboxylic acid, 202 parts of lactose, 80 parts of corn starch, and 20 parts Amijel B011 are blended in a suitable mixer.
2. The mixture is granulated to a heavy paste with water and the moist mass is passed through a No. 12 screen. It is then dried overnight at 110°F.
3. The dried granules are passed through a No. 16 screen and transferred to a suitable mixer. The calcium stearate is added and mixed until uniform.
4. The mixture is compressed at a tablet weight of 410 mg using tablet punches having a diameter of approximately three-eighth inch. (Tablets may either flat or biconvex and may be scored if desired.)

EXAMPLE 38

Parenteral Formulation
Each 1 cc ampul contains:

| | Per cc |
|---|---|
| 8-Cyano-1,2-dihydro-3(4H)-dibenzofuran carboxylic acid | 10.2 mg (2 percent excess) |
| Methyl Paraben, U.S.P. | 1.8 mg |
| Propyl Paraben, U.S.P. | 0.2 mg |
| Sodium Hydroxide, U.S.P. q.s. ph | 9.0 |
| Water for Injection, U.S.P. q.s. ad | 1.0 cc |

Procedure (For 10,000 cc):
1. In a clean glass or glass-lined vessel, 8,000 cc of Water for Injection are heated to 90°C. It is then cooled to 50°–60°C, and 18 grams of methyl paraben and 2 grams of propyl paraben are added and dissolved with stirring. The solution is then allowed to cool to room temperature.
2. The 102.0 grams of 8-cyano-1,2-dihydro-3(4H)-dibenzofurancarboxylic acid is added under an atmosphere of nitrogen and stirred until completely dispersed.
3. The Sodium Hydroxide was added as a 10 percent solution until the pH was adjusted to 9.0 plus or minus 0.1, and the drug is completely dissolved.
4. Sufficient Water for Injection is then added to make a total volume of 10,000 cc.
5. This solution is then filtered through an 02 Selas candle, filled into suitable size ampuls, gassed with nitrogen and sealed. It is autoclaved at 10 lbs PSI for 30 minutes.

EXAMPLE 39

Suppository Formulation

|  | Per 1.3 Gm Suppository |
|---|---|
| 8-Cyano-1,2-dihydro-3(4H)-dibenzofuran-carboxylic acid | 0.025 mg |
| Wecobee M* | 1.230 mg |
| Carnauba Wax | 0.045 gm |

*E. F. Dew Company, 522 Fifth Avenue, New York, New York

Procedure 1. 123 Parts of Wecobee M and 4.5 parts of carnauba wax are melted in a suitable size glass-lined container (stainless steel may also be used), mixed well and cooled to 45°C.
2. 2.5 Parts of 8-cyano-1,2-dihydro-3(4H)-dibenzofurancarboxylic acid, which has been reduced to a fine powder with no lumps, is added and stirred until completely and uniformly dispersed.
3. The mixture is poured into suppository molds to yield suppositories having an individual weight of 1.3 gms.
4. The suppositories are cooled and removed from molds, and individually wrapped in wax paper for packaging. (Foil may also be used.)

We claim:
1. A compound, 3-(4-chlorophenoxy)-4-oxo-cyclohexanecarboxylic acid ethyl ester.
2. A compound, 3-(4-chlorophenoxy)-4-oxo-cyclopentanecarboxylic acid methyl ester.

* * * * *